United States Patent [19]

Britten-Kelly et al.

[11] 4,383,943
[45] May 17, 1983

[54] ACETALDEHYDE ETHYL ISOEUGENYL ACETAL PERFUME COMPOSITIONS

[75] Inventors: Michael R. Britten-Kelly, Metuchen, N.J.; Edward J. Shuster, Brooklyn; Odd Hansen, Jackson Heights, both of N.Y.

[73] Assignee: Fritzsche Dodge & Olcott Inc., New York, N.Y.

[21] Appl. No.: 309,378

[22] Filed: Oct. 7, 1981

[51] Int. Cl.³ .............................................. A61K 7/46
[52] U.S. Cl. ................................ 252/522 R; 568/592
[58] Field of Search ..................... 252/522 R; 568/592

[56] References Cited

U.S. PATENT DOCUMENTS 3,948,814  4/1976  de Rijke .......................... 252/522 R

OTHER PUBLICATIONS

Arctander, S., "Perfume and Flavor Chemicals" Pub. by Author, Montclair, N.J., (1969), Monographs 1370 & 1371.

*Primary Examiner*—John F. Niebling
*Attorney, Agent, or Firm*—Cooper, Dunham, Clark, Griffin & Moran

[57] ABSTRACT

The present invention relates to the novel compound acetaldehyde ethyl isoeugenyl acetal, useful as a fragrance material. The invention also provides a method of preparing this compound from isoeugenol and fragrance compositions which include the compound.

2 Claims, No Drawings

ACETALDEHYDE ETHYL ISOEUGENYL ACETAL PERFUME COMPOSITIONS

BACKGROUND OF THE INVENTION

Isoeugenol, described in the literature (S. Arctander, "Perfume and Flavor Chemicals", published by the author, Montclair (1969); compound no. 1370) as having a "mild and sweet, deep-floral, very tenacious odor with great warmth", is extensively used in perfume compositions. However, this compound is sensitive to alkali and discolors certain products. To overcome these disadvantages, derivatives of isoeugenol such as isoeugenyl acetate (Arctander compound no 15), described as a "fruity-balsamic, warm and faintly spicy"; isoeugenyl formate (Arctander compound no 1374), described as "fresh-green, sweet-woody"; and isoeugenyl phenylacetate (Arctander compound no. 1376), described as "intensely sweet, Vanilla-Clove-like" are sometimes employed; however, these derivatives are not generally suitable as substitutes for isoeugenol.

Acetaldehyde eugenyl methyl acetal (Arctander compound no. 1371) has been suggested as a modifier for eugenol; however, it is reputedly not as spicy nor as powerful as eugenol.

THE INVENTION

The subject of the present invention is the novel compound acetaldehyde ethyl isoeugenyl acetal, which has the following formula:

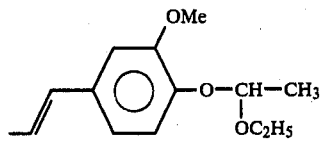

This compound retains the same odor characteristics as isoeugenol. It is slightly weaker when fresh but is longer-lasting than isoeugenol, cleaner, sweeter and more floral as it dries. The performance in fragrance compositions is excellent, enhancing the sweet, floral, spicy notes with less harshness than isoeugenol. The performance in soap is good, and the product does not discolor after six months storage.

The compound of the present invention is clearly a valuable fragrance material which possesses many of the useful characteristics of isoeugenol, and is of great interest in its own right.

The preparation of acetaldehyde ethyl isoeugenyl acetal may be accomplished by addition of a catalytic amount of concentrated hydrochloric acid to a mixture of isoeugenol and ethyl vinyl ether as described in the following Example.

EXAMPLE I

Preparation of Acetaldehyde Ethyl Isoeugenyl Acetal

Scheme:

A 5-liter flask equipped with a stirring motor, thermometer, and reflux condenser was charged with isoeugenol (820 g, 5 mol) and vinyl ethyl ether (1440 g, 20 mol). Concentrated HCl (2 ml) was added in one portion with stirring. An immediate exothermic reaction followed with a temperature rise from 25° to 40° in 20 min. The temperature then fell slowly to room temperature over 7h. (see Note.)

After standing overnight, the reaction mixture was stirred with 5% sodium bicarbonate (200 ml). The organic phase was separated, washed with water (250 ml), and the excess vinyl ethyl ether recovered by fractionation through a 30 cm column packed with $\frac{1}{4}''$ Raschig rings. The recovered ether amounts to 899 g (GLC 99.5%), b.p. 37°–38° C.

The residue was then fractionated through the same column at reduced pressure, taking fractions as follows:

| Fraction | Weight | T vap | T pot |
|---|---|---|---|
| 1 | 35.1g | 110–126° | 158–161° |
| 2 | 15.4g | 126–128° | 161–163° |
| 3 | 23.4g | 128° | 163–164° |
| 4 | 297.1g | 128° | 164–165° |
| 5 | 514.8g | 128° | 165° |
| 6 | 114.3g | 128° | 165° |
| 7 | 89.3g | 128° | 165–170° |
| 8 | 27.4g | 128–130° | 170–178° |

On the basis of an organoleptic evaluation, fractions 4 through 8 were bulked as the product.

Yield: 1043 g (88%).

Note: Progress of reaction was monitored by IR, observing the disappearance of the —OH peak.

The following Examples illustrate perfume compositions prepared according to this invention using the acetaldehyde ethyl isoeugenyl acetal of Example I.

EXAMPLE II

| Perfume composition "carnation" | |
|---|---|
| Heliotropine extra FCC | 20 parts by weight |
| Oil basil sweet FCC extra | 10 |
| Oil ylang extra | 30 |
| Cinnamon leaf FCC Ceylon | 3 |
| Phenyl ethyl alcohol FCC | 80 |
| Phenyl propyl alcohol FCC | 40 |
| Hexyl salicylate | 187 |
| Eugenol FCC extra | 430 |
| Rose absolute | 40 |
| | 840 parts by weight |

This mixture was divided and further compounded as follows:

A

| | |
|---|---|
| Above mixture | 420 parts by weight |
| Isoeugenol FCC | 80 |
| | 500 parts by weight |

B

| | |
|---|---|
| Above mixture | 420 parts by weight |

| Perfume composition "carnation" | |
|---|---|
| Acetaldehyde ethyl isoeugenyl acetal | 80 |
| | 500 parts by weight |

The compounds A and B were evaluated and compared. It was found that the compound of Example I enhances the sweet, floral, spicy character, both fresh and on dryout, without the harshness imparted by isoeugenol.

EXAMPLE III

| Perfume composition "dianthine" | |
|---|---|
| Eugenol FCC extra | 500 parts by weight |
| Cinnamic alcohol FCC | 40 |
| Benzyl isoeugenol | 20 |
| Hexyl salicylate | 50 |
| Oil ylang extra | 65 |
| Ethyl vanillin FCC | 3 |
| Phenylethyl alcohol FCC | 80 |
| Phenylethyl salicylate FCC | 50 |
| Benzyl acetate FCC | 25 |
| 1-Citronellol | 10 |
| Geraniol FCC 96–98% | 10 |
| Oil carrot seed FCC extra | 7 |
| | 920 parts by weight |

This mixture was divided and further compounded as follows:

A
| | |
|---|---|
| Above mixture | 460 parts by weight |

| Perfume composition "dianthine" | |
|---|---|
| Isoeugenol FCC | 40 |
| | 500 parts by weight |
| B | |
| Above mixture | 460 parts by weight |
| Acetaldehyde ethyl isoeugenyl acetal | 40 |
| | 500 parts by weight |

The compositions A and B were evaluated and compared. It was found that the compound of the present invention enhances the floral topnote, whereas isoeugenol flattens it and makes the odor harsher and rougher. On dry out the sweet spicy floral character is very evident in compound B, while the isoeugenol in compound A tends to decrease the floral note and enhance the clove leaf character.

What is claimed is:

1. The compound acetaldehyde ethyl isoeugenyl acetal, having the formula:

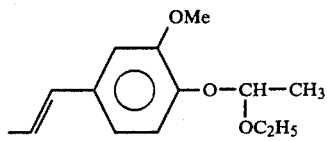

2. A fragrance composition which comprises an amount of the compound of claim 1 effective to impart fragrance thereto in combination with conventional fragrance ingredients.

* * * * *